United States Patent [19]

Schubert

[11] Patent Number: 4,918,000

[45] Date of Patent: Apr. 17, 1990

[54] MULTI-COLOR LABELING OF DIFFERENT ANTIGENS IN A BIOLOGICAL SYSTEM

[76] Inventor: Walter Schubert, Schiefener Weg 14, D-5208 Eitorf, Fed. Rep. of Germany

[21] Appl. No.: 780,958

[22] Filed: Sep. 27, 1985

[51] Int. Cl.[4] .............................................. G01N 33/53
[52] U.S. Cl. .......................................... 435/7; 435/1; 435/4; 435/29; 435/810; 424/3; 436/503; 436/536; 436/546; 436/547; 436/548; 436/800; 436/805; 436/808
[58] Field of Search .................. 435/7, 810, 1, 4, 29; 436/536, 503, 547, 546, 548, 800, 805, 808; 424/3

[56] References Cited

U.S. PATENT DOCUMENTS 4,672,028  6/1987  Olson ................................ 435/810

*Primary Examiner*—Robert J. Warden
*Assistant Examiner*—Stephen C. Wieder
*Attorney, Agent, or Firm*—Robert Wells

[57] ABSTRACT

A method of multi-color labeling at least two antigens present in a tissue such as non-liquid tissue or body fluids, with the aid of different antibodies is improved by introducing between the labeling of the first antigen and the labeling of the second antigen, and between labeling of the second and that of any further antigen, at least once a treatment with a non-immune normal serum and optionally other agents blocking any binding sites remaining free in the tissue after a last-preceding labeling step.

37 Claims, No Drawings

MULTI-COLOR LABELING OF DIFFERENT ANTIGENS IN A BIOLOGICAL SYSTEM

BACKGROUND OF THE INVENTION

This invention relates to a method of multi-color labeling at least two antigens being simultaneously present in a common biological system, with the aid of a corresponding number of different antibodies. In a second aspect the invention relates to a novel kit for carrying out the aforesaid method.

Fluorescene-optical multi-color labeling of different antigens in the same biological system, in particular animal, and especially human "tissue" (meaning non-liquid tissue as well as blood) is of special importance for investigating diagnostic or medical scientific problems.

For instance, such labeling is useful in the precise identification of lymphocyte subpopulations in pathologically and non-pathological tissues such as inflammatory myopathies, or auto-immune thyreoiditis, normal and pathologically changed lymphoid tissues, infiltrations or inflammatory changes in malignant and non-malignant tumors and metastases of malignant tumors, blood and cerebral fluid in pathological and non-pathological states diagnoses of immunodeficiency syndromes in blood such as AIDS and others listed on page 28 of a publication entitled "Ortho-mune (R), Monoklonale Antikörper, Zelltypisierung in Peripherblut and lymphatischem Gewebe" by Dr. Molter GmbH, D-6903 Neckergemünd, Federal Republic of Germany, and many other fields of biological investigation.

Hitherto, it was only possible to effect multi-markings of blood, but not of other tissues with very costly and highly complicated laser analyzers such as a FACS analyzer or a Spectrum 3 analyzer which are available, due to their cost, in only a very limited number of medical institutions.

Methods published by William E. Gathings, Ph.D. and others in 1977 in the European Journal of Immunology 7, page 804 under the title of "Immunofluorescent Studies of Development of Pre-B Cells, B-Lymphocities and Immunoglobulin Isotype Diversity in Humans" have been reported by Becton Dickinson Labor Systems' "Monoclonal Antibody Source Book" published subsequently in Heidelberg in the Chapter "Methods—Immunofluorescence Staining of Cell Surfaces—Cytocentrifuge Preparations" comprise two-color indirect immunofluorescence preparations of human peripheral blood with the following reagents:

(1) Fluorescine(FITC) or rhodamine (RITC) labeled mouse monoclonal antibody specific for membrane antigen, as well as, for double-marking:

(1a) unconjugated or biotin-labeled mouse monoclonal antibody specific for membrane antigen, followed by (1b) anti-mouse Ig FITC/RITC) or followed by (1c) Avidin FITC/RITC.

I have found that this method will not work for double-marking when (1a) is unconjugated and (1b) is anti-mouse Ig FITC/RITC, when the unconjugated antibody of (1a) is of the same immunoglobulin class as directly conjugated antibody of (1), as this method yields unspecific double markings.

Moreover, biotin-labeled mouse monoclonal antibody of (1a) followed by avidin FITC/RITC of (1b) as obtained from Becton and Dickinson fails to afford specific double markings.

However, even when using in the last combination an avidin FITC/RITC of different origin, I obtained only weak and quickly fading fluorescent markings. The weakness and fading were particularly pronounced in the green (FITC) markings.

Another method of fluorescence double marking of primary antibodies from the same animal species has been published by Amersham Buchler GmbH and Co. KG, D-3300 Braunschweig in "The biotin-streptavidin system" published in April 1985 (penultimate sheet). This method always leads to unspecific fluorescence double markings of the first incubation sequence.

Furthermore, D. Y. Mason, Z. Abdulazig, B. Falini and H. Stein assert on page 119 in an article entitled "Double Immunoenzymatic Labelling" published in "Immunocytochemistry, Practical Applications in Pathology and Biology", by G. Wright, Bristol and Boston, 1983 that it is "not possible to perform double labeling by" use of class- or subclass-specific antibodies (FIG.7.6) "if the two primary antibodies are of the same subclass. Since many monoclonal antibodies are of the Ig Gl subclass this represents an important potential limitation" of this known method.

OBJECTS AND SUMMARY OF THE INVENTION

It is an important object of the present invention to provide a method enabling such multi-labeling, in particular double or triple labeling of tissues, which can be carried out not only in laboratories with highly expensive detection apparatus such as laser analysers, and by highly trained specialists in this field, but in ordinary hospital and even individual immunologist's laboratories equipped with a fluorescence microscope or, in the case of immunoenzymatic labelling, only a standard laboratory microscope by normally trained medical technical assistants, and even untrained personnel.

Another object of my invention is to provide a method and kit for improved detection of two, three, four or even more antigens in a tissue, completely avoiding any spurious labeling.

A further object of my invention is to provide a method and kit for performing double labeling of two antigens using monoclonal antibodies of the same species and even the same subclass, for instance the IgG 1, IgG 2a, IgG 2b or other subclasses of immunoglobulins.

A still further object of my invention is to provide a method and kit for an especially potent double immunofluorescent labeling suitable for detecting and selectively showing small amounts of different overlapping or super-imposed imposed antigens on the same tissue structures, such as a membrane or introcellular particles.

These objects and others that will become apparent from the further description hereinafter are attained, in accordance with a first aspect of my invention by the improvement in a method of multi-color labeling at least two different antigens being simultaneously present in a common biological system, with the aid of a corresponding number of different antibodies, comprising:

(a) adding to an animal tissue containing at least one first antigen (AG I) and a second antigen (AG II), a first primary antiserum being a first solution, in an aqueous, antigen- and antibody-compatible solvent, of at least one primary antibody, active against said first antigen, in an amount effectively immunologically reacting with said first antigen, free from a moiety labeling any antigen in an optically detectable manner, (b) adding to the tissue resulting from Step (a) at least one secondary antiserum, being a solution in the same kind of solvent, of at least one secondary antibody immunologically reacting with said at least one antigen I-specific primary antibody, at least one such secondary antiserum containing at least one of said secondary antibodies being conjugated with a first detecting moiety selected from
(i) a first labeling radical conjugated directly with said secondary antibody, and
(ii) a first labeling radical conjugated with said secondary antibody via a first labeling effect-enhancing bridge member; thereby labeling said first antigen in an optically detectable manner, (c) adding to the resulting treated tissue from Step (b) a second primary antiserum of a random animal species and being a second solution, in an aqueous, antigen- and antibody-compatible solvent, of at least one antigen II-specific primary antibody immunologically reactive with said second antigen (AG II), said at least one different primary antibody being completely free from activity against any antibodies and any normal sera introduced previously into said tissue, and being conjugated with a second detecting moiety selected from
(i) a second labeling radical conjugated directly with said antigen II-specific primary antibody, and
(ii) a second labeling radical conjugated with said antigen II-specific primary antibody via a second labeling effect-enhancing bridge member;

said second detecting moiety affording a second labeled antigen (AG II) being readily optically distinguishable from the first-labeled antigen (AG I) obtained with said first detecting moiety; which comprises (d) the at least one secondary antibody in said at least one secondary antiserum of Step (b) containing free binding sites in excess of those becoming occupied by said at least one primary antibody of Step (a)

said second detecting moiety being free from cross reactivity with said first detecting moiety, and (e) adding to the tissue after Step (b) and prior to Step (c), still containing free binding sites being capable of acting against any subsequently introduced antibodies or against subsequently introduced bridge members, from at least one specific non-immune fraction up to the entire non-immune normal serum, of the same animal species as said second primary antiserum of Step (c), in an amount sufficient for blocking all those free binding sites remaining from the last-preceding step; and when any of said free binding sites are capable of acting against any subsequently introduced bridge members, adding further a blocking agent for blocking said last-mentioned sites;

with the PROVISO that Step (e) follows Step (c) only when all antibodies of Steps (a), (b) and (c) are free from mutual cross reactivities, and with the further PROVISO that when the animal species from which said first primary antiserum added in Step (a) is produced is a first subclass of a determined species such as the mouse, and the first secondary antibody contained in said secondary antiserum from said second animal species, added in Step (b) is conjugated with a first labeling radical via a first labeling effect-enhancing bridge member, and the animal species yielding the antigen (AG II)-specific antibody contained in the second primary antiserum added in Step (c) is an animal such as a mouse from another subclass of the said one or another animal species than mouse, and said last-mentioned antibody is free from a detecting moiety, then follows the step of:

(f) adding to the tissue resulting from Step (c) being free from any cross reactivity a third secondary antiserum containing a third secondary antibody being reactive with said antigen (AG II)-specific antibody, said third secondary antibody being conjugated with said second labeling radical directly or via said second labeling effect-enhancing bridge member, said second bridge member being free from reactivity with any previously or subsequently added bridge member, and Step (e) is omitted.

"Biological systems" as used in this specification and claims, are animal, and particularly human, "tissues" including non-liquid tissues as well as blood and other body fluids.

Sera and antisera of animal species most readily available in commerce and recommended for use in the method according to the invention are those of the mouse, rat, goat, sheep and rabbit. For instance, as the first non-immune normal serum used in Step (AA), infra, there is recommended, for instance, the use of goat serum or a mixture of goat and rabbit, or goat and human serum.

As the antibody of the second species used in Step (B), infra, there is recommended a mouse monoclonal antibody suitable for reacting with a determined antigen.

Antigen- and antibody-compatible solvents are, for instance, phosphate-buffered salines of a pH of about 7.3 to 7.6 such as the phosphate-buffered saline PBS of pH 7.4, or tris-buffered saline TBS, of pH 7.6, described on page 20 in "Monoclonal Antibodies" published by DAKO Corporation, Santa Barbara, California 93103 in January 1984.

I did not obtain any better results by adding to the aforesaid salines an albumin buffer solution recommended by earlier investigators, when labeling lymphocyte surface antigens in cryostat sections of inflamed skeletal muscle tissue.

By "primary" are meant those being specifically reactive with an antigen, while "secondary" antibodies mean antibodies which are specifically reactive with another antibody previously added to the tissue being labeled.

By a "detecting moiety" there is meant a chemical grouping being linked with an antibody molecule by a chemically conjugated bond.

Such detecting moiety consists either of a labeling radical alone and directly bonded to the remainder of the antibody molecule; or they can consist of a labeling-effect enhancing bridge member which is conjugated directly with the said antibody molecule and with which there is in turn conjugated the aforesaid labeling radical.

Such labeling radical can be the radical of a fluorochrome such as fluorescin isothiocyanate or rhodamine.

Only three of the presently known fluorochromes excited by ultraviolet light are easily optically distinguishable in a fluorescence microscope or in a laser microscope, built by Zein AG, D-7082 Oberkochen, Fed. Rep. of Germany, by the use of excitation, band-path, emission filters etc.

On the other hand, the labeling radical can be that of an enzyme being capable of catalizing a specific substrate reaction in which the resulting product can be made visible via a colored product obtained in turn at the site of the antigen. Such enzymes are, for instance, peroxidase, alkaline phosphatase, glucosoxidase gelactosidase and others.

The use of fluorochrome radicals is preferred by me because antigen superimposed in different strata of the same structure or located adjacent each other, but so closely that, when they are labeled immunoenzymatically, they can not be seen separately in a standard light microscope, cannot safely identified by the observer's eye, leading to erroneous interpretations of the results.

However, when they are labeled with fluorochromes which are of sufficiently different emissions separable by filters, they can be readily distinguished in a fluorescence microscope or a laser microscope; even antigens being located one above the other in different superimposed strata can be made selectively visible after dyeing, for instance, one of them green and the other red, and then viewing the structure through the fluorescence microscope using first an appropriate filter for green and then another for red emission.

When photographing by double exposure such structure, being selectively filtered in the fluorescence microscope, there is obtained a photograph in which the superimposed green and red spots yield a yellow spot, all spots in which the two antigens are not superimposed, appearing green or red. This permits to distinguish in the tissue being investigated three different types of cells or the like biological units, one bearing a first antigen, another bearing a second antigen, and a third one bearing both antigens superimposed with one another.

Labeling of three antigens simultaneously present in the same structure permits identification of up to six different types of biological units.

The only instance known to me, where such fluorochrome identification of to antigens in the same structure has been achieved, was done in the Mayo Clinic in Rochester, Minnesota, with a not generally applicable method of carrying out the incubation steps, as reported by Arahata and Engel in "Annals of Neurology" Vol. 16 No. 2, pages 193–208 and ibidem, pages 209–215 (August 1984). This known method, however, suffers from the drawback of a very weak primary fluorescence of the obtained labeled tissue sites which can be improved by very sophisticated and complicated measures requiring a highly specialized technology not to be found in normal hospital and similar laboratories.

"Binding sites" of antibodies are capable of immunologically reacting with antigens or antibodies at epitopes which are more or less reaction-avid sites of the antibody molecule generally not by means of covalent chemical bonds but, for instance, Van der Waals bond and hydrogen bridges.

"Binding sites" of labeling effect-enhancing bridge members are capable of entering with a very strong affinity into bonds with active sites on another molecule, closely resembling that of chemical bonds.

Blocking agents capable of blocking such free binding sites of the above-mentioned bridge members are, for instance, haptens such as avidin which can block biotin (Vitamin H), p-aminobenzoyl glycine, p-aminobenzoyl glutamic acid, arsanilic acid and others.

There will be described hereinafter preferred modes of carrying out the method according to the invention in practice.

According to a first such mode, applied to a tissue which contains besides the first and second antigens, also at least one n-th antigen different from the former ones; the Step (e) is carried out following one of Steps (b) and (c), and the improvement according to the invention further comprises:

(f) adding to the tissue resulting from the later-applied one of Steps (c) and (e), an n-th primary antiserum, other than the first and second primary sera, containing, dissolved in a solvent as defined, a primary antibody specially active against an n-th antigen other than said first and second antigens;

the tissue resulting from said last applied Step being completely free from binding sites active against the antigen n-specific primary antibody and against an subsequently introduced defecting system;

the n-th antigen-specific primary antibody being conjugated with an n-th detecting moiety selected from (i) an labeling radical conjugated directly with the last-mentioned antibody, and (ii) a labeling radical conjugated with the last-mentioned antibody via a labeling effect-enhancing bridge member;

said labeling radical of said n-th detecting moiety affording an n-th antigen labeled in an optically distinguishable manner from all antigens labeled previously with an earlier-introduced labeling agent.

Preferably, the first primary antiserum of Step (a) and the non-immune normal serum of Step (e) are obtained from the same animal species.

In a more preferred mode of operation, the improved method according to the invention comprises the incubation steps of (AA) adding to the animal tissue containing the at least two different antigens, in an effective amount, a first non-immune, heat inactivated normal serum of an animal of a first animal species, different from the species from which the primary antibody is produced, and (A) adding to the resulting serum-treated tissue from Step (AA) the first primary antiserum of Step (a) contains an antigen (AG I)-specific primary antibody produced in an animal of at least one determined immuno-globulin class of a second animal species and being free from reactivity with the first normal serum, in an amount effectively reacting with a first one of the different antigens.

The more preferred mode of operation further comprises (B) adding to the tissue resulting from Step (A) a secondary antiserum of another than the second animal species and containing at least one first secondary antibody being free from reactivity with the first normal serum of Step (AA), and being active against the first antibody of the second animal species;

(D) adding to the tissue resulting from Step (B) a second secondary antiserum of a random animal species and containing at least one further secondary antibody active against the first secondary antibody added in Step (B);

at least one of the secondary antibodies introduced by Steps (B) and (D), and preferably both, being conjugated with a first detecting moiety, and at least one of the said secondary antibodies having free binding sites in excess of those occupied by the first primary antibody, and being capable of binding at least one antigen II-specific primary antibody.

The first secondary antibody of Step (B) can also be free from conjugation with a first detecting moiety, but then the further secondary antibody of Step (D) must be conjugated with such first detecting moiety.

In the most preferred mode of operation, the tissue obtained from Step (A) is treated further with Step (B), supra but not with Step (D), and at least one of the secondary antibodies in the antiserum of (B) must be conjugated with the said first detecting moiety, and at least one of the secondary antibodies must have free binding sites in excess of those occupied by the first primary antibody, which free binding sites are capable of binding antigen II-specific primary antibodies; the resulting tissue is then treated further by:

(E) adding to the tissue from Step (B) an agent consisting essentially of from at least one inactive immunoglobulin subclass up to the entire non-immune normal serum, of the same animal species as the second primary antiserum of Step (c), supra, in an amount sufficient for blocking all those free binding sites remaining from the last-preceding Step (B); and when any of the free binding sites are capable of acting against any subsequently introduced bridge members, a blocking agent for blocking the last-mentioned sites must also be added;

(C) adding to the resulting treated tissue from Step (E) a second primary antiserum of a random animal species and being a second solution, in an aqueous, antigen- and anti-body-compatible solvent, of at least one antigen II-specific primary antibody immunologically reactive with the second antigen (AG II). This at least one antigen II-specific primary antibody should be completely free from activity against any antibodies and any normal sera introduced previously into the tissue, and must be conjugated with a second detecting moiety which affords a second labeled antigen (AG II) being readily optically distinguishable from the first labeled antigen (AG I) obtained with the first detecting moiety.

In order to obtain stronger labeling especially in the case of the labeling radical of the first detecting moiety being a fluorochrome a second secondary antiserum of Step (D) is added to the tissue resulting from Step (B), which second secondary antiserum contains at least one further secondary antibody conjugated with a first detecting moiety having the same color as the first detecting moiety conjugated with the first secondary antibody of Step (B); the further secondary antibody of (D) being free from reactivity with the normal serum of Step (AA) and being capable of immunologically reacting with the first secondary antibody of Step (B).

In the further treatment of the tissue ($E_1$) the non-immune normal serum of Step (e) can be added to the tissue resulting from Step (D), and the further secondary antibody of (D) should be free from reactivity with said normal serum of Step (AA). Alternatively, ($C_1$) the second primary antiserum containing the at least one antigen II-specific antibody of Step (c) can be added to the tissue resulting from Step ($E_1$); or ($E_2$) the non-immune normal serum of Step (e) can be added directly to the tissue resulting from Step (B), before or concurrently with the second secondary antiserum of Step (D).

When the secondary antiserum of Step (D) is added to the tissue resulting from treatment with Step ($E_2$), the further secondary antibody of (D) should be free from reactivity with the non-immune normal sera of Steps (AA) and (E), and be reactive with the first secondary antibody of Step (B) as well as being conjugated with a first detecting moiety of the same color as any first detecting moiety conjugated with the first secondary antibody of Step (B).

In a further variation ($C_2$) the second primary antiserum containing the at least one antigen II-specific antibody of Step (c) which is non-reactive with any normal sera and any antisera added previously to said tissue, can be added to the tissue resulting from Step (D). Or, according to the variation, ($C_3$) the second primary antiserum of a random animal species containing the at least one antigen II-specific antibody is added to the tissue resulting from Step ($E_2$).

In a particularly simple mode of operation, the antigen I-specific primary antibody of Step (A), the normal serum of Step (E) and the antigen II-specific primary antibody from Step (C) can all be produced from the same animal species of a Type I; moreover, the normal serum of Step (AA) and the first secondary antibody of Step (B) can both be produced from the same animal species, but of a Type II being different from that of type I.

Results of clear labeling are further greatly improved by (H) washing the treated tissue after each of the preceding steps (a) through (f) or any partial steps explained hereinbefore or hereafter with an aqueous buffered saline solution having a pH-value of about 7.3 to 7.6.

In all those cases where only double labeling is to be achieved, the method according to the invention will end with Step (c) and Step (g) can be dispensed with.

However, when a tissue contains more than two antigens to be labeled, then, subsequent to the above-explained Steps (a) to (e) of the method according to the invention, there should follow the additional steps of (F) adding to the tissue resulting from one of Steps (C), ($C_1$), ($C_2$) and ($C_3$), at least one specific non-immune fraction up to the entire non-immune normal serum of a random animal species, in an amount sufficient for blocking any free binding sites remaining from Stage (C), and (G) adding, in the case of at least one different antigen (AGx) other than the first and second antigens being present in the tissue, to the tissue resulting from the Step (F) at least one further antiserum of the same animal species as that from which the normal serum of (F) is produced, the last-mentioned antiserum being a solution, in an aqueous antigen- and antibody-compatible solvent, of a further antigen (AGx)-specific antibody, different from any other previously added antibody, of a random animal species, in an amount sufficient for effectively reacting with the further different antigen (AGx); the further antigen (AGx)-specific antibody must be active against the different antigen (AGx) and must also be free from reactivity with any other previously added antibody and must be conjugated with a further detecting moiety affording a color different from those of the first and second detecting moieties, and being selected from (i) a different labeling radical conjugated directly with the antigen (AGx)-specific antibody, and (ii) a different labeling radical conjugated with the antigen (AGx)-specific antibody via a bridge member enhancing the labeling effect of the said different labeling radical, While any previously introduced bridge members of the first and second detecting moieties must be free from reactivity with the last-mentioned bridge member or such reactivity must have been blocked prior to Step (G).

When the animal species from which the first primary antiserum added in Step (A) is obtained is a first subclass of the mouse, and the first secondary antibody contained in the secondary antiserum from the second animal species, added in Step (B) is conjugated with a first labeling radical via a first labeling effect-enhancing bridge member; moreover, the animal species yielding the antigen (AG II)-specific antibody contained in the second primary antiserum added in Stage (c) is a mouse from another subclass than the first one or another animal species than the mouse, and the last-mentioned antibody is free from a detecting moiety, then there can follow the step of further treating the tissue by:

(K) adding to the tissue resulting from Step (c) being free from any cross reactivity a third secondary antiserum containing a third secondary antibody being reactive with the antigen (AG II)-specific antibody, the third secondary antibody being conjugated with the second labeling radical directly or via the second labeling effect-enhancing bridge member, the second bridge member being free from reactivity with any previously or subsequently added bridge member, while Step (E) can then be omitted.

According to another aspect of the invention, there is provided a kit for carrying out a method of multi-color labeling at least two different antigens, namely a first antigen (AG I) and a second antigen (AG II), being simultaneously present in a common biological system, with the aid of a corresponding number of different antibodies, which kit comprises as components:

(AA) a non-immune normal serum from a first animal species;

(A) a first primary antiserum from a second animal species and being a first solution, in an aqueous, antigen- and antibody-compatible solvent, of at least one (AG I)-specific primary antibody, which antibody is free from a moiety labeling any antigen in an optically detectable manner;

(B) a secondary antiserum from a random animal species, being a solution, in an aqueous, antigen- and antibody-compatible solvent, of at least one secondary antibody acting against the at least one (AG I)-specific primary antibody, at least one such (AG I)-specific primary antibody being conjugated with a first detecting moiety;

(E) a non-immune normal serum from an animal species other than the first one;

(C) at least one second primary antiserum from the same species as the component (E) and containing at least one (AG II)-specific antibody, free from immunological reactivity with any of components (AA), (A) and (B), and being conjugated with a second detecting moiety being free from reactivity with the first detecting moiety; and (H) an aqueous physiologically acceptable buffer solution having a pH of about 7.3 to 7.6.

In preferred kits, one or several of the following details are recommend:

(1) The second primary antiserum (C) is of the second animal species.

(2) The at least one antibody contained in Component (B) is polyclonal and the antibodies of Components (A) and (C) are monoclonal.

(3) The antisera of Components (A) and (C) are of the same species and monoclonal.

(4) The antibodies in Components (A) and (C) are free from the mouse, Component (AA) is a non-immune normal serum selected from goat serum, rabbit serum, sheep serum, human serum and mixtures of at least two thereof; and the secondary antiserum of Component (B) is a goat antiserum, rabbit antiserum or a sheep antiserum.

(5) The antiserum of Component (B) is of the first animal species other than human antiserum.

(6) The normal serum (AA) contains from 0 to about 98% by weight of a physiologically acceptable buffer having a pH-value of about 7.3 to 7.6, and there is present in the undiluted state per kit unit at least about one millimeter of this serum.

(7) The first primary antiserum (A) contains from 0 to about 90% of a physiologically acceptable buffer having a pH-value of about 7.3 to 7.6, and, in the undiluted state, per kit unit, at least about 50 micrograms of antibody in about 1.0 milliliter phosphate buffered saline containing about 0.2% gelatin and about 0.1 sodium azide, the saline having a pH-value of about 7.3 to 7.6.

(8) The secondary antiserum (B) contains from about 0 to 90% of a physiologically acceptable buffer having a pH-value of about 7.3 to 7.6, and, in the undiluted state, per kit unit, at least about 100 micrograms of antibody in 1.0 milliliter of physiologically acceptable liquid medium.

(9) The second primary antiserum (C) is of a random animal species and contains from about 0 to 90% of a physiologically acceptable buffer having a pH-value of about 7.3 to 7.6, and, in the undiluted state, per kit unit, at least about 50 micrograms of antibody in about 1.0 milliliter of physiologically acceptable liquid medium.

(10) The non-immune normal serum (E), of the same animal species as the donor of the second primary antiserum (C), contains from about 0 to 90% by weight of a physiologically acceptable buffer having a pH-value of about 7.3 to 7.6, and, in the undiluted state, per kit unit at least about one milliliter.

(11) The Component (B) comprises (B') as a first sub-component thereof, a first secondary antiserum of another than the second animal species as defined under (B), supra, and containing at least one first secondary antibody being active against said first primary antibody of Component (A), and, (D) as a second sub-component thereof, a second secondary antiserum of a random animal species and containing at least one further secondary antibody active against the first secondary antibody of the first secondary antiserum of (B');

at least one of the subcomponents (B') and (D) containing the antibody therein conjugated with the said second detecting moiety.

(12) The first secondary antiserum of (B') is of an animal species other than the second species, and the second secondary antiserum is produced from an animal species other than the first and second species, each of the above first and second secondary sera containing from 0 to about 95% of a physiologically acceptable buffer having a pH-value of about 7.3 to 7.6, and, in undiluted state, per kit unit at least about 100 micrograms grams of antibody in 1.0 milliliter of physiologically acceptable liquid medium.

(13) (G) a third primary antiserum of a random animal species containing a third antigen (AG III)-specific antibody, free from any immunological reactivity with any of components (AA), (A), (B), (B'), (C), (D), and (E) present in the kit, and being conjugated with a third detecting moiety free from reactivity with the first and second detecting moieties.

(14) (J) a fourth primary antiserum of a random animal species containing a fourth antigen (AG IV)-specific antibody, free from any immunological reactivity with any of components (AA), (A), (B), (B'), (C), (D), (E) and (G), present in the kit, and being conjugated with a fourth detecting moiety free from reactivity with the said first, second and third detecting moieties.

In the two last-mentioned kits according to the invention, from one to at most three of the detecting moieties contain a fluorochrome radical, and remaining moieties are enzyme radicals affording different optically visible labeling.

In another preferred embodiment of the last-mentioned three types of kits, Component (C) is constituted by (C') a first subcomponent being a second primary antiserum containing at least one (AG II)-specific primary antibody free from immunological reactivity with any of components (AA), (A), and (B) and being unconjugated with any detecting moiety, this second primary antiserum of (C') being from a different immunoglobulin class or subclass of the second animal species or from an animal species different from the second species; and (F) as a second subcomponent, another secondary antiserum from an animal species other than that from which the antiserum (C') is produced, this last-mentioned secondary antiserum containing a different secondary antibody being specifically reactive with the respective class, subclass or species of the (AG II)-specific primary antibody and being conjugated with a second detecting moiety non-reactive with, and being optically distinguishable from the first detecting moiety.

the Components (A), (B), (C) and (F) as far as present in this kit being free from cross reactivities therebetween.

EXAMPLES

The following non-limitative examples illustrate the method according to the invention further. Percentages given therein are by weight unless expressly stated otherwise. Temperatures are given in degrees Celsius (centigrades); all examples are carried out at 20° C. unless another temperature is mentioned.

EXAMPLE 1

A cryostat section from a human skeletal muscle, musculus gastrocnemius, is placed on a glass object support lamina and left uncovered, then fixed in ice-cold acetone for 10 minutes, air-dried and then into a slide-carrier glass cuvette filled with phosphate buffer saline (PBS) for 2 minutes. The slide is then taken out, residual liquid is removed by careful shaking, and the area on the slide around the section is completely cleaned with a cloth of any liquid. The section is not covered with a cover slip.

STEP AA: The thus prepared slide is then placed on an object carrier and introduced horizontally into a dark humidity box. The section on the slide inside the dark box is then covered completely with 30 microliters (mcl) of a non-immune normal goat serum sold by ORTHO Diagnostic Systems GmbH, D-6903 Neckergemünd, Germany (a), which serum is diluted to 4% weight/volume and the slide is then left for 30 minutes in the closed box.

The slide is than taken out of the box, excess liquid is removed, and the slide is placed in a PBS-filled cuvette for 2 minutes, excess buffer is removed, the slide is cleaned around the section and placed again horizontally into the humidity box. (Intermediary Treatment).

STEP A: The section on the slide is then covered with 30 mcl of a solution of commercially available mouse-anti-human monoclonal antibody OKT 8 (meaning: against the ORTHOKung-T-lymphocyte No. 8) in PBS prepared by me in a volume ratio of 1:10. After 30 minutes incubation in the dark humidity box, the slide is taken out and the above-described intermediary treatment is repeated.

STEP B: The slide is then returned to the dark humidity box, the section on the slide is covered therein with 30 mcl of a 1:20 (volume ratio) diluted solution in PBS of fluorescein isothiocyanate (FITC)-conjugated ORTHO goat-anti-mouse (GAM) serum commercially available from (a), supra, and incubated in the dark box for 30 minutes. The intermediary treatment of the slide removed from the dark box is repeated as described hereinbefore.

STEP E: In the dark humidity box, the section is then covered with 30 mcl of an undiluted non-immune normal mouse serum, commercially available from Camon Labor Service GMbH, D-6200 Wiesbaden, Germany, and incubated in the dark for 30 minutes. The slide is then taken out of the box in the dark, excess liquid is removed, and the slide is then placed, still in the dark, into PBS in a cuvette and left therein for 30 minutes. The slide is then cleaned about the section in the light, and is then placed again into the dark humidity box.

STEP C: The section is then covered in the dark with 30 mcl of phycoerythrin (PE)-conjugated monoclonal mouse-anti-human antibody (against the antigen) Leu 3a, commercially available from Becton Dickinson Labor System, D-6900 Heidelberg, Germany (c), diluted by me with PBS to a volume ratio of 1:10.

While the above-described intermediary washing treatment is carried out for 2 minutes in the dark, a fresh covering agent consisting of 1 mg of p-phenylenediamine in 1 ml of glycerol gelatin is prepared, and the section on the slide is covered with a small amount of this agent (having a temperature of 37° C.) and then with a cover slip.

When observed under a fluorescence microscope with oil immersion, the antigen OKT 8 showed green fluorescence and the other antigen, Leu 3a, showed red-orange fluorescence, while the background was not completely dark but showed a greyish-brown hue; this permits judging of the morphology of the unlabeled tissue, which is not possible when the background tissue is completely black. In fact, the black background resulting in several known labeling methods was the reason why immunoenzymatic labeling was preferred to fluorochrome labeling up till now.

When the slide is then stored at −85° C., the fluorescence of the preparation will remain unchanged for at least four months or even much longer. Observation of the 4-month old slide stored at the said temperature, showed in a fluorescence microscope fully satisfactory colors, and fading under excitation with ultraviolet light is less then when the slide is observed immediately after preparation. The improved fluorescence of both labeled antigens can be observed already when storing the freshly prepared section overnight at a temperature below 0° C., and especially at −85° C.

Examples 2-5

The table shown hereinafter presents further examples of double labeling sections of the same human skeletal tissue and by the same method steps as described in detail in Example 1. Commercially available agents used in the following examples are sold by the companies designated by either (a), (b) or (c) listed supra, or by
(d) DAKO Corporation, Santa Barbara, Calif. 93103;
(e) Behring-Werke AG, D-6800 Mannheim, Germany;
(f) Amersham Buchler GmbH and Co. Kg, D-3300 Braunschweig, Germany;
TRITC means rhodamine triisocyanate.

Example 7

A cryostat section from a human lymphnode tissue is prepared and mounted in the same manner as described in Example 1.

Step AA is carried out with fetal calf serum (b) concentration: undilutes, treatment time 30 minutes.

Step A is carried out with mouse-anti-human Leu 11, commercially available from Becton-Dickinson Labor Systems, (c), supra, diluted 1:10, with an incubation time of 30 minutes.

Step B is carried out with goat-anti-mouse (GAM)-FITC (a), diluted 1:20, for 30 minutes.

Step D: The slide is then placed in the humidity box and the section thereon is covered with 30 microliters of biotinylated rabbit-anti-goat antibody (b), diluted 1:20, for 20 minutes, and after PBS-washing, the slide is again covered with streptavidin-FITC (f), diluted 1:20, for 30 minutes.

In Step E, mouse normal serum is used 1:2 for 30 minutes.

After the same washing step as in Example 1, the slide is further treated in the same manner, but with mouse-anti-Leu 1 phycoerythrin (PE) diluted 1:10 for 30 minutes.

The weak antigen LEU 11 is labeled a satisfactorily strong green, and Leu 1 a pronounced red-orange.

Example 8

Example 3 is repeated and the still uncovered slide resulting from Step (C) is washed in PBS and reintroduced into the dark humidity box.

STEP G: The slide is then covered with 30 mcl of 1:5-diluted biotinylated mouse-anti-Leu 4 antibody for 30 minutes and further incubated in the dark humidity box with 30 mcl of 1:20-diluted streptavidin-Texas Red.

The finished section shows on the tissue changed by inflammation the first antigen, OKT 4, green-fluorescent, the second antigen, Leu 2a, red-orange, and the

| Example No. | STEP AA serum | STEP AA dilution incub. time (min.) | STEP A serum | STEP A dilution incub. time (min.) | STEP B serum | STEP B dilution incub. time (min.) | STEP E serum | STEP E dilution incub. time (min.) | STEP C serum | STEP C dilution incub. time (min.) |
|---|---|---|---|---|---|---|---|---|---|---|
| 2 | goat | 100% 20 | anti OKT 3 mouse- | 1:5 20 | GAM-FITC (a) | 1:20 20 | mouse | 1:10 20 | mouse Leu 2a-PE | 1:10 20 |
| 3 | rabbit | 1:10 30 | anti OKT 4 mouse | 1:10 30 | GAM-FITC | 1:30 30 | mouse | 1:2 30 | mouse Leu 2a-PE | 1:5 30 |
| 4 | sheep | 1:10 40 | mouse anti OKT 11 | 1:8 60 | rabbit AM-FITC | 1:15 40 | mouse | 1:10 40 | mouse Leu 15-PE | 1:10 30 |
| 5 | human | 1:5 20 | rabbit anti-human myoglobin (d) | 1:20 30 | goat anti-rabbit-FITC (b) | 1:40 20 | rabbit | 100% 30 | rabbit anti-neuron-specific enolase (d) + biotin-streptavidin Texas Red (f) | 1:20 30 1:20 30 |
| 6 | bovine serum-albumin BSA (e) | 100% 30 | sheep-anti-human immuno-globulin (Ig) G (b) | 1:10 30 | donkey anti-sheep Ig G-TRITC (b) | 1:50 40 | sheep | 1:30 40 | sheep anti-human Ig M-FITC (b) | 1:20 30 |

The rabbit anti-neuron specific enolase, commercially available from Dako Corp. is conjugated with an equivalent amount of Biotin and the resulting conjugate is then further reacted with an equivalent amount of Streptavidin-Texas Red.

third antigen, Leu 4, red fluorescent, which are distinguishable by using appropriate filters, including a Texas Red-filter, manufactured by Carl Zeiss AG, D-7082 Oberkochen, Germany.

Example 9

A cryostat section of an inflamed human muscle, biceps brachii, is prepared and treated in a Step (AA) in the same manner as described in Example 1, with following washing with PBS.

The slide is then treated in exactly the same manner as described in Step A of Example 1, wherein the antibody against OKT8 is IgG.

Step B of Example 1 is then repeated, however the antiserum used therein is biotinylated sheep-anti-mouse Ig F(ab')$_2$ fragment (f), diluted 1:20, for 30 minutes.

The slide is then covered in the dark humidity box with 30 mcl of streptavidin Texas Red solution (f), diluted 1:20, and also treated for 30 minutes.

STEP D: After washing with PBS, the slide is then incubated in the dark humidity box with 30 mcl of rat-anti-human mono-clonal immune-answer associated (Ia-like) antigen Ig M-antibody (b), diluted 1:10, treatment time 30 minutes, followed again by PBS-washing.

The washed slide is then covered in the dark humidity box with 30 mcl of FITC-conjugated sheep-anti-rat anti-Ig M antiserum (b) diluted 1:20, the treatment lasting 30 minutes. The resulting double labeled slide could be examined in a fluorescence microscope. The first antigen OKT8 is labeled red fluorescent, and the second antigen Ia is labeled green fluorescent.

However, the treatment of the slide is to be continued in order to label a third antigen present in the tissue. Following Step E, the slide is incubated in the dark humidity box during 30 minutes with 30 mcl of 1:10, diluted PE-conjugated monoclonal mouse-anti-human Leu 3a antibody solution commercially available from Becton-Dickinson GmbH (c).

The triple-labeled slide is then finished as described in Example 1.

The labeled third antigen, Leu 3a, shows orange-red fluorescence.

Example 10

A cryostat slide from the same human tissue treated in Example 1 is used and

Step AA was applied as described in that Example, but in the light. The biologically active substance used in Step AA and B as well as other intermediate treatment stages were taken from an "Ortho-OKT-Kit" sold by Ortho Diagnostic Systems (a).

Step A: The slide obtained from Step AA and washed is reintroduced into the light humidity box and was covered for 30 minutes with 30 mcl of 1:10 diluted monoclonal mouse-anti-human anti-actin (a cytoskeletal protein) (f).

Step B$_1$: The PBS-washed slide was then covered in the light humidity box with 30 mcl of a 1:20-diluted solution of peroxidase-conjugated F(ab')$_2$-sheep-anti-mouse immunoglobulin (f) incubated for 30 minutes and then washed with PBS.

Step B$_2$: A substrate solution for reaction with the enzyme is prepared by adding to a solution of diaminobenzidine (DAB) in PBS having a concentration of 0.5 mg of DAB per milliliter PBS, a sufficient amount of hydrogen peroxide affording a concentration of 0.02% $H_2O_2$ in the substrate solution, which is then filtered.

The slide obtained from Step (B$_1$), supra, is then covered with 30 mcl of the aforesaid filtered substrate solution and a brown precipitate is formed at the site of the first antigen being labeled, actin. The precipitation reaction is arrested by placing the slide in distilled water, and the slide is then washed with PBS in a cuvette for 2 minutes.

Step E: The slide is then treated as described in Step E of Example 1, including the final PBS-washing for 30 minutes.

Step C: The slide is then treated in the light humidity box by covering it with 30 mcl of a biotinylated monoclonal mouse-anti-human antibody against Leu 2a (c), diluted 1:10 and incubating it for 30 minutes.

The PBS-washed slide is then covered with 30 mcl of a 1:20 solution, in PBS, of streptavidin—galactosidase complex (f) for 30 minutes.

The slide is then washed in PBS and then covered with a substrate solution prepared by adding to a solution of 5-bromo-4-chloro-3-indoyl-galactoside (BCIG) dissolved in PBS and having a concentration of 0.5 milligram/milliliter BCIG, containing further, per milliliter of the solution, one milli-Mol of magnesium chloride, 3 milli-Mol of potassium ferricyanide and 3 milli-Mol of potassium ferrocyanide; the solution which has a pH-value of 7.4, is used without further dilution and the section is incubated therein for 20 minutes.

A blue precipitate is formed at the sites of the second antigen, Leu 2a. The slide is then placed in distilled water and covered with a cover slip in an aqueous mounting medium.

Example 11

Example 10 was repeated up to and including Step E:

Step C: The slide is then treated in the dark humidity box with a 1:10-diluted solution of PE-conjugated monoclonal mouse-anti-human antibody against Leu 2a, the incubation time being 30 minutes.

The second antigen, Leu 2a, is labeled a fluorescent red-orange. The slide is then washed with PBS for 2 minutes and then covered with a cover slip using as mounting medium a mixture of p-phenylenediamine with glycerol-gelatin in a concentration of one mg per milliliter of the mixture.

The simultaneous observation of the red orange-labeled Leu 2a-sites and the brown actin sites under ultraviolet light with concurrent transillumination with appropriately adjusted bright-field light is made possible by the fact that the labeled actin shows no noticeable auto-fluorescence under ultraviolet light.

This example is, therefore, recommended for tissues in which one of the antigens is of low concentration.

Example 12

Human blood is freshly drawn and heparinized. An amount of 10 ml of this blood is brought into a test tube charged with 4 to 5 ml of plastic beads coated with one spoon tip of iron powder, thereby absorbing the macrophages and granular leucocytes on the beads. The contents of the test tube are then incubated at 37° C. in a shaking bath.

A dextran solution is obtained by dissolving 5 g of dextran in 100 ml of physiological sodium chloride saline, and an amount of 6 ml of the dextran solution is then added to the test tube and the mixture is allowed to settle for 60 minutes with the test tube being held inclined at an angle of 45° while incubating the contents at 37° C. The supernatant is removed and carefully layered on to a sterile density gradient material (e.g. Ficoll Hypaque, sold by Pharmacia, D-7800 Freiburg im Breisgau, Germany) in a proportion of one part of Ficoll to 2 parts of the cell suspension; the resulting supernatant contains only lymphocytes. The mixture of density gradient and cell suspension is then centrifuged at 700 G for 20 minutes.

The band layer between the Ficoll layer and the sera layer is then carefully removed with a Pasteur pipette and the band layer containing the lymphocytic cells is washed with PBS for 5 minutes. A lymphocyte shape-stabilizing agent (e.g., Media 199, sold by GIBCO, D-7514 Eggenheim, Germany) is then added to the washed cell suspension, and the concentration of the mixture is adjusted with PBS to 4 million cells per milliliter suspension.

STEP A: 200 mcl of the adjusted stabilized cell suspension are passed into another test tube and 5 mcl of undiluted monoclonal mouse-anti-human antibody (against) OKT 8 are added thereto; the resulting mixture is incubated for 30 minutes in and ice/-water bath (about 0° C.) while shaking briefly every ten minutes.

Centrifuging Step: 2 ml of the stabilizing agent, supra, are added to the incubated suspension, and the latter is then centrifuged at 300 G for 5 minutes at +4° C., the suspension is then briefly shaken to re-suspend the cells, and centrifuging is repeated.

STEP B: After re-suspension of the cells, 100 mcl of FITC-conjugated goat-anti-mouse serum are added and the resulting suspension is placed in a dark space at 20° C. The centrifuging step is then repeated and then, 100 mcl of 1:5 diluted non-immune normal mouse serum are added and then incubated in the dark for 30 minutes. The centrifuging step is then repeated.

STEP C: 5 mcl of an undiluted primary solution of phycoerythrin-conjugated monoclonal mouse-anti-human antibody (against) Leu 3a, sold by (c), are added to the suspension which is then shaken briefly and incubated in the dark for 30 minutes in an ice/water bath, the brief shaking being repeated every 10 minutes. The centrifuging step is then repeated, the supernatant is separated from the sediment, and the latter is suspended in a small amount of the lymphocyte shape-stabilizing agent.

A drop of the resulting suspension is placed on a slide and covered with a cover slip, and the labeled lymphocytes are then counted in a fluorescence microscope using FITC-adjusted and PE-adjusted filters.

In general, labeled membranes in a tissue being investigated such as lymphocyte membranes cannot be made visible by the described method, if the tissue is formaldehyde-fixed and embedded in paraffin. Therefore, cryostat sections of tissue shock-frozen in iso-pentane floating in liquid nitrogen are preferably used in the method according to the invention.

Double labeling with the aid of fluorochromes affords particularly satisfactory results on tissues which contain little connective tissue, because the latter tissue becomes itself fluorescent even when no antigens are labeled therein. This auto-fluorescence may disturb the labeling of antigens present on such connective tissue. Therefore, double labeling of such tissue is better done using immunoenzyme techniques in the method according to the invention.

I claim:

1. A method for multicolor-labeling at least two different antigens simultaneously present in a common biological system, with the aid of a corresponding number of different antigen-specific antibodies, comprising
    (a) adding to an animal tissue containing at least a first antigen and a second antigen, at least a first primary antibody, active against said first antigen and free from a moiety labeling any antigen in an optically detectable manner, in an amount effectively immunologically reacting with said first antigen;
    (b) adding to the tissue resulting from step (a) at least a first secondary antibody immunologically reacting with said first primary antibody and containing free binding sites in excess of those occupied by said first primary antibody, said first secondary antibody being conjugated with a first detecting moiety selected from the group consisting of:
    (i) a first labeling radical conjugated directly with said first secondary antibody, and
        (ii) a first labeling radical conjugated with said first secondary antibody via a first labeling effect-enhancing bridge member; thereby labeling said first antigen in an optically detectable manner;
    (c) adding to the treated tissue resulting from step (b) and still containing free binding sites capable of acting against any subsequently introduced antibodies or against subsequently introduced bridge members, at least one inactive immunoglobulin subclass of a non-immune normal serum from a given animal species, in an amount sufficient for blocking all free antibody-specific binding sites remaining from step (b) and,
    (d) adding to the treated tissue resulting from step (c) a second primary antibody from the same animal species as said non-immune normal serum,
    said second primary antibody being immunologically reactive with said second antigen, completely free from activity against any antibodies and any normal sera introduced previously into said treated tissue, and conjugated with a second detecting moiety free from cross reactivity with said first detecting moiety and being selected from the group consisting of:
        (i) a second labeling radical conjugated directly with said second primary antibody, and
        (ii) a second labeling radical conjugated with said second primary antibody via a second labeling effect-enhancing bridge member; thereby labeling said second antigen as optically distinguishable from said first antigen labeled with said first detecting moiety.

2. The method of claim 1, wherein said tissue contains at least one further antigen different from said first and second antigens, and further comprising:
    (f) adding to the tissue resulting from step (d) a third primary antibody specifically active against said further antigen;
    said tissue resulting from step (d) completely free from binding sites active against said third primary antibody and against a subsequently introduced detecting system;
    said third primary antibody being conjugated with a third detecting moiety selected from the group consisting of:
        (i) a third labeling radical conjugated directly with said third primary antibody, and
        (ii) a third labeling radical conjugated with said third primary antibody via a third labeling effect-enhancing bridge member;

said labeling radical of said third detecting moiety affording said further antigen labeled in an optically distinguishable manner from all antigens labeled previously with an earlier-introduced labeling agent.

3. The method of claim 2, further comprising (H) washing the treated tissue after each of the preceding steps (a) through (d) with an aqueous buffered saline solution having a pH-value of about 7.3 to 7.6.

4. The method of claim 1, wherein said first primary antibody of step (a) and said immunoglobulin subclass of step (c) are obtained from the same animal species.

5. The method of claim 1, comprising the incubation steps of:
(AA) adding to said animal tissue containing said at least two different antigens, in an effective amount, a first non-immune, heat inactivated normal serum of an animal of a first animal species, different from the species from which said primary antibody is produced, and
(A) adding to the resulting serum-treated tissue from step (AA), said first primary antibody produced in an animal of at least one determined immunoglobulin class of a second animal species and being free from reactivity with said first normal serum, in an amount effectively reacting with said first antigen.

6. The method of claim 5, further comprising:
(B) adding to the tissue resulting from step (A) said first secondary antibody of another than said second animal species free from reactivity with said first normal serum of step (AA) and being active against said first antigen of said second animal species, and
(D) adding to the tissue resulting from step (B) a further secondary antibody active against said first secondary antibody added in step (B),
at least one of said secondary antibodies introduced by steps (B) and (D) being conjugated with said first detecting moiety,
and at least one of said secondary antibodies having free binding sites in excess of those occupied by said first primary antibody, and being capable of binding at least said second primary antibody.

7. The method of claim 6, wherein a second secondary antibody of step (D) is added to the tissue resulting from step (B), said second secondary antibody being conjugated with a first detecting moiety having the same color as said first detecting moiety conjugated with said first secondary antibody of step (B); said further secondary antibody of (D) being free from reactivity with said normal serum of step (AA) and being capable of immunologically reacting with said first secondary antibody of step (B).

8. The method of claim 7, wherein ($E_1$) said immunoglobulin of step (c) is added to the tissue resulting from step (D).
said further secondary antibody of (D) being free from reactivity with said normal serum of step (AA).

9. The method of claim 8, wherein ($C_1$) said second primary antibody of step (d) is added to the tissue resulting from step ($E_2$).

10. The method of claim 5, further comprising
(B) adding to the tissue resulting from step (A) a first secondary antibody from an animal other than said second animal and being free from reactivity with said first normal serum of step (AA) and being active against said first primary antibody of said second animal species,
at least one of said secondary antibodies introduced by step (B) being conjugated with said first detecting moiety,
and at least one of said secondary antibodies having free binding sites in excess of those occupied by said first primary antibody;
(E) adding to the tissue from step (B), still containing free binding sites being capable of acting against any subsequently introduced antibodies or against subsequently introduced bridge members, from at least one inactive immunoglobulin subclass up to the entire non-immune serum, of the same animal species as said second primary antibody of step (d), in an amount sufficient for blocking all those free binding sites remaining from the last preceding step (B); and
when any of said free binding sites are capable of acting against any subsequently introduced bridge members, adding further a blocking agent for blocking said last-mentioned sites; and
(c) adding to the resulting treated tissue from step (E) a second primary antibody of a given animal species reactive with said second antigen,
said second primary antibody being completely free from activity against any antibodies and any normal sera introduced previously into said tissue, and being conjugated with a second detecting moiety,
said second detecting moiety affording a second labeled antigen being readily optically distinguishable from said first labeled antigen obtained with said first detecting moiety.

11. The method of claim 10, wherein ($E_2$) said immunoglobulin of step (c) is added directly to the tissue resulting from step (B) alone or concurrently with said second secondary antibody of step (D).

12. The method of claim 11, wherein said further secondary antibody of step (D) is added to the tissue resulting from treatment with step ($E_2$), said further secondary antibody of (D) being free from reactivity with said non-immune normal sera of steps (AA) and (E), and being reactive with said first secondary antibody of step (B) as well as being conjugated with a first detecting moiety of the same color as said first detecting moiety conjugated with said first secondary antibody of step (B).

13. The method of claim 12, wherein ($C_2$) said second primary antibody of step (d) being nonreactive with any normal sera and any antisera added previously to said tissue, is added to the tissue resulting from step (D).

14. The method of claim 11, wherein ($C_3$) said second primary antibody of said animal other than said second animal is added to the tissue resulting from step ($E_2$).

15. The method of claim 14, wherein said first primary antibody of step (A), said normal serum of step (E) and said second primary antibody from step (C) are all produced from the same animal species.

16. The method of claim 15, wherein said normal serum of step (AA) and said first secondary antibody of step (B) are both produced from the same animal species of a different type.

17. The method of claim 6, wherein said first secondary antibody of Step (B) is free from conjugation with a first detecting moiety and said further secondary antibody of Step (D) is conjugated with a first detecting moiety.

18. A method for multi-color-labeling of at least two different antigens simultaneously present in a common biological system, with the aid of a corresponding number of different antibodies, comprising:
  (a) adding to an animal tissue containing at least a first antigen and a second antigen at least a first primary antibody from a first subclass of a first animal species in an amount effectively immunologically reacting with said first antigen, said first primary antibody being free from a moiety labeling any antigen in an oprically detectable manner;
  (b) adding to the tissue resulting from step (a) at least a first secondary antibody from a second animal species, immunologically reacting with said first primary antibody and being conjugated with a first detecting moiety consisting of a first labeling radical and a first labeling effect-enhancing bridge conjugating said first labeling radical with said first secondary antibody, thereby labeling said first antigen in an optically detectable manner;
  (c) adding to the tissue resulting from step (b) a second primary antibody from a second subclass of said first animal species or from said second or another animal species, being free from a detecting moiety and second antigen-specific; and
  (d) adding to the tissue resulting from step (c) when free from any cross reactivity, a third secondary antibody reactive with said second primary antibody and being conjugated with a second detecting moiety selected from the group consisting of:
    (i) a third labeling radical conjugated directly with said third secondary antibody; and
    (ii) a third labeling radical conjugated with said third secondary antibody via a third labeling effect-enhancing bridge member, said third bridge member being free from reactivity with any previously or subsequently added bridge member; thereby labeling said second antigen as optically distinguishable from said first antigen labeled with said first detecting moiety.

19. A method for multi-color-labeling at least two different antigens simultaneously present in a common biological system, with the aid of a corresponding number of different antibodies, comprising:
  (a) adding to an animal tissue containing at least a first antigen and a second antigen, at least a primary antibody active against said first antigen and free from a moiety labeling any antigen in an optically detectable manner, in an amount effectively immunologically reacting with said first antigen;
  (b) adding to the tissue resulting from step (a) at least a first secondary antibody immunologically reacting with said first primary antibody and being conjugated with a first detecting moiety selected from the group consisting of:
    (i) a first labeling radical conjugated directly with said first secondary antibody, and
    (ii) a first labeling radical conjugated with said first secondary antibody via a first labeling effect-enhancing bridge member; thereby labeling aid first antigen in an optically detectable manner;
  (d) adding to the treated tissue resulting from step (b) a second primary antibody from a given animal species, immunologicaly reactive with said second antigen and/being completely free from activity against any antibodies introduced previously into said treated tissue, and being conjugated with a second detecting moiety free from cross reactivity with said first detecting moiety an being selected from the group consisting of:
    (i) a second labeling radical conjugated directly with said second primary antibody, and
    (ii) a second labeling radical conjugated with said second primary antibody via a second labeling effect-enhancing bridge member; thereby labeling said second antigen as optically distinguishable from said first antigen; and
  (e) adding to the treated tissue resulting from step (d) and still containing free binding sites capable of acting against any subsequently introduced antibodies or against subsequently introduced bridge members at least one inactive immunoglobulin subclass of a non-immune normal serum, of the same animal species as said second primary serum, in an amount sufficient for blocking all those free antibody-specific binding sites.

20. The method of claim 19, wherein said tissue contains at least one further antigen different from said first and second antigens, and further comprising:
  (f) adding to the tissue resulting from step (e) a third primary antibody specifically active against said further antigen;
  said tissue resulting from step (e) being completely free, apart from said further antigen, from other binding sites active against said third antibody or a subsequently introduced detecting system;
  said third primary antibody being conjugated with a third detecting moiety selected from the group consisting of:
    (i) a third labeling radical conjugated directly with said third primary antibody, and
    (ii) a third labeling radical conjugated with said third primary antibody via a third labeling effect-enhancing bridge member;
  said labeling radical of said third detecting moiety affording said further antigen labeled in a manner optically distinguishable from all antigens labeled previously with an earlier-introduced labeling agent.

21. A kit for carrying out a method for multi-color labeling of at least two different antigens, namely a first antigen and a second antigen, being simultaneously present in a common biological system, with the aid of a corresponding number of different antibodies, said kit comprising as components:
  (AA) a first container having a non-immune normal serum from a first animal species;
  (A) a second container having a first primary antiserum from a second animal species and being a first solution, in an aqueous, antigen- and antibody-compatible solvent, of at least one first antigen specific primary antibody, said antibody being free from a moiety labeling any antigen in an optically detectable manner;
  (B) a third container having a secondary antiserum from a random animal species, being a solution, in an aqueous, antigen- and antibody-compatible solvent, of at least one secondary antibody acting against said at least one first antigen specific primary antibody, at least one such first antigen specific primary antibody being conjugated with a first detecting moiety;
  (E) a fourth container having a non-immune normal serum from an animal species other than said first one;

(C) a fifth container having at least one second primary antiserum from the same species as said component (E) and containing at least one second antigen specific antibody, free from immunological reactivity with any of containers (AA), (A) and (B), and being conjugated with a second detecting moiety being free from reactivity with said first detecting moiety; and (H) a sixth container having an aqueous physiologically acceptable buffer solution having a pH of about 7.3 to 7.6.

22. The kit of claim 21, wherein said second primary antiserum (C) is of a second animal species.

23. The kit of claim 1, wherein the at least one antibody contained in Component (B) is polyclonal and the antibodies of Components (A) and (C) are monoclonal.

24. The kit of claim 23, wherein the antibodies in Components (A) and (C) are mouse antibodies, Component (AA) is a non-immune normal serum selected from the group consisting of goat serum, rabbit serum, sheep serum, human serum and mixtures of at least two thereof; and the secondary antiserum of Component (B) is selected from the group consisting of goat antiserum, rabbit antiserum or a sheep antiserum.

25. The kit of claim 21, wherein the antisera of Components (A) and (C) are of the same animal species and monoclonal.

26. The kit of claim 21, wherein said antiserum of Component (B) is of said first animal species other than human antiserum.

27. The kit of claim 21, wherein said normal serum (AA) contains from 0 to about 98% by weight of a physiologically acceptable buffer having a pH-value of about 7.3 to 7.6, and in the undiluted state per kit unit at least about one milliliter is present.

28. The kit of claim 27, wherein said first primary antiserum (A) contains from about 0 to about 90% of a physiologically acceptable buffer having a pH-value of about 7.3 to 7.6, and, in the undiluted state, per kit unit, at least about 50 micrograms of antibody in about 1.0 milliliter phosphate buffered saline containing about 0.2% gelatin and 29. The kit of claim 28, wherein said secondary antiserum (B) contains from about 0 to 90% of a physiologically acceptable buffer having a pH-value of about 7.3 to 7.6, and, in the undiluted state, per kit unit, at least about 100 micrograms of antibody in 1.0 milliliter of physiologically acceptable liquid medium.

30. The kit of claim 29, wherein said second primary antiserum (C) is of a random animal species and contains from about 0 to 90% of a physiologically acceptable buffer having a pH-value of about 7.3 to 7.6, and, in the undiluted state, per kit unit, at least about 50 micrograms of antibody in about 1.0 milliliter of physiologically acceptable liquid medium.

31. The kit of claim 30, wherein said non-immune normal serum (E), of the same animal species as the donor of said second primary antiserum (C), contains from about 0 to 90% by eight of a physiologically acceptable buffer having a pH-value of about 7.3 to 7.6, and, in the undiluted state, per kit unit at least about one milliliter.

32. The kit of claim 21, wherein said Component (B) comprises (B') as a first sub-component thereof, a first secondary antiserum of another than said second animal species as defined under (B), supra, and containing at least one first secondary antibody being active against said first primary antibody of Component (A), and, (D) as a second sub-component thereof, a second secondary antiserum of a random animal species and containing at least one further secondary antibody active against said first secondary antibody of said first secondary antiserum of (B');

at least one of said subcomponents (B') and (D) containing said antibody therein conjugated with said second detecting moiety.

33. The kit of claim 32, wherein said first secondary antiserum of (B') is of an animal species other than said second species, and contains from 0 to about 95% of a physiologically acceptable buffer having a pH-value of about 7.3 to 7.6, and, in undiluted state, per kit unit at least about 100 micrograms of antibody in 1.0 milliliter of physiologically acceptable liquid medium, and said second secondary antiserum is produced from an animal species other than said first and second species, and contains from 0 to about 95% of a physiologically acceptable buffer having a pH-value of about 7.3 to 7.6, and, in undiluted state, per kit unit at least about 100 micrograms of antibody in 1.0 milliliter of physiologically acceptable liquid medium.

34. The kit of claim 21, further comprising (G) a seventh container having a third primary antiserum of a random animal species containing a third antigen specific antibody, free from any immunological reactivity with any of components (AA), (A), (B), (B'), (C), (D), and (E) present in said kit, and being conjugated with a third detecting moiety free from reactivity with said first and second detecting moieties.

35. The kit of claim 21, further comprising (J) a seventh container having a fourth primary antiserum of a random animal species containing a fourth antigen specific antibody, free from any immunological reactivity with any of components (AA), (A), (B), (B'), (C), (D), (E) and (G), present in said kit, and being conjugated with a fourth detecting moiety free from reactivity with said first, second and third detecting moieties.

36. The kit of claim 35, wherein from one to at most three of said detecting moieties contain a fluorochrome radical, and remaining moieties are enzyme radicals affording different optically visible labeling.

37. The kit of claim 21, wherein said Component (C) is constituted by (C') a first subcomponent being a second primary antiserum containing at least one second antigen specific primary antibody free from immunological reactivity with any of components (AA), (A), and (B) and being unconjugated with any detecting moiety, said second primary antiserum of (C') being from a different immunoglobulin class of subclass of the second animal species or from an animal species different from said second species; and (F) as a second subcomponent, another secondary antiserum from an animal species other than that from which said antiserum (C') is produced, said last-mentioned secondary antiserum containing a different secondary antibody being specifically reactive with the respective class, subclass or species of said second antigen specific primary antibody and being conjugated with a second detecting moiety non-reactive with, and being optically distinguishable from said first detecting moiety, said Components (A), (B), and (C') and (F) being free from cross reactivities therebetween.

* * * * *